United States Patent [19]

Riess et al.

[11] Patent Number: 5,582,813
[45] Date of Patent: Dec. 10, 1996

[54] IODINE-CONTAINING FLUOROCARBON CONTRAST AGENTS

[75] Inventors: Jean G. Riess; Leila Zarif; Veronique Sanches; Jacques Greiner, all of Nice, France

[73] Assignee: Alliance Pharmaceutical Corp., San Diego, Calif.

[21] Appl. No.: 188,396

[22] Filed: Jan. 27, 1994

[30] Foreign Application Priority Data

Jan. 28, 1993 [FR]  France ................................. 93 00866

[51] Int. Cl.$^6$ .......................... A61K 49/04; A61K 51/12; B01J 13/00
[52] U.S. Cl. ...................... 424/1.89; 252/312; 252/315.1; 514/744; 514/746; 514/938
[58] Field of Search ................................. 252/312, 315.1; 514/744, 746, 832, 833, 938; 424/9.45, 1.89, 9.4

[56] References Cited

U.S. PATENT DOCUMENTS

| | | | |
|---|---|---|---|
| 3,778,381 | 12/1973 | Rosano et al. | 252/312 X |
| 3,989,843 | 11/1976 | Chabert et al. | 514/672 |
| 4,058,573 | 11/1977 | Knell | 570/172 |
| 4,367,216 | 1/1983 | Mutzel et al. | 424/9.452 |
| 4,569,784 | 2/1986 | Moore | 252/315.1 |
| 4,613,708 | 9/1986 | Riess et al. | 514/832 X |
| 4,769,241 | 9/1988 | Heldebrant et al. | 424/7 |
| 4,987,154 | 1/1991 | Long, Jr. | 514/832 X |
| 5,114,703 | 5/1992 | Wolf et al. | 424/9.32 |
| 5,264,220 | 11/1993 | Long, Jr. et al. | 514/832 X |

FOREIGN PATENT DOCUMENTS

| | | |
|---|---|---|
| 0115943 | 1/1984 | European Pat. Off. . |
| 0289187 | 11/1988 | European Pat. Off. . |
| 2132473 | 11/1972 | France . |
| 2679150 | 1/1993 | France . |
| 9100110 | 1/1991 | WIPO . |

OTHER PUBLICATIONS

Brace, Neal O. (1982) Some approaches to the synthesis of fluorinated alcohols and esters. II. use of f-alkyl iodides for the synthesis of f-alkyl alkanols. Journal of Flourine Chemistry 20:313–327.

Chen, Qing–Yen et al. (1987) Studies on fluoroalkylation and fluoroalkoxylation. Part 24. Magnesium–induced Single electron transfer in reactions of fluoroalkyl iodides with alkenes and alkynes. Journal of Fluorine Chemistry 36:149–161.

Deray, G. et al. (1991) Risques rénaux lors de l'administration de produits de contraste iodés ches les patients diabétiques. Diabetes & Metabolisme (Paris) 17:379–382.

Ishihara, T. et al. (1986) New efficient palladium–catalyzed perfluoroalkylation of carbon–carbon multiple bonds with f-alkyl iodides. An expedient route to f-alkylated alkyl and alkenyl iodides. Chemistry Letter 1895–1896.

Long, Carl D. et al. (1989) Preparation and application of highly concentrated perfluoroctylbromide fluorocarbon emulsions. Blood 441–442.

Long, Carl D. p. 139 in "Preparations, properties and industrial applications of organofluorine compounds" R. E. Banks, Ed. (Ellis Horwood Ltd., Chinchester, U.K. (1982).

Westhoff–Bleck, Mechthild, et al. (1991) The adverse effects of angiographic radiocontrast media. Drug Safety 6 (1):28–36.

J. G. Riess, Presents trends in fluorocarbon–based blood substitutes. Life Support Sciences 2(4):273–275 (1984).

*Primary Examiner*—Richard D. Lovering
*Attorney, Agent, or Firm*—Knobbe, Martens, Olson & Bear

[57] ABSTRACT

The present invention relates to nonterminally iodinated fluorinated compositions. The compositions, including, dispersions, emulsions, microemulsions, and gels are useful for biomedical applications, particularly radiography and scintigraphy. The compounds used in the invention preferably have the following general formula:

$$R_FCH=CIR^1$$

wherein, $R_F$ is a linear, branched, or cyclic first fluorocarbon radical, having 2 to 12 carbon atoms in which 50 to 100% of the hydrogen atoms have been replaced by fluorine atoms; and $R^1$ is selected from the group consisting of a second fluorocarbon radical and a hydrocarbon radical, wherein, the second fluorocarbon radical is linear, branched, or cyclic, having 2 to 12 carbon atoms in which 50 to 100% of the hydrogen atoms have been replaced by fluorine atoms; and the hydrocarbon radical is linear, branched, or cyclic, having 2 to 14 carbon atoms.

40 Claims, 1 Drawing Sheet

IODINE-CONTAINING FLUOROCARBON CONTRAST AGENTS

BACKGROUND OF THE INVENTION

1. Field of the Invention

The present invention relates to dispersions, emulsions, microemulsions, gels and compositions including an organic iodized fluorocarbon compound, for biomedical use. Such compositions are useful notably in diagnosis, and particularly as contrast enhancement agents in radiography and scintigraphy.

2. Background of the Art

Conventional contrast enhancement agents utilized in diagnostic procedures are from the following classes: hydrosoluble agents, lipidic agents, or brominated perfluorocarbon agents. Each of these classes of agents has attendant problems. For example, iodinated hydrosoluble agents have a short intravenous persistence due to their rapid diffusion in the tissues. Therefore, the time in which the examination can be undertaken is significantly reduced, and successive injections are often necessary.

Moreover, these agents provoke side effects ranging from anaphylactic reactions to cardiovascular distress. See Deray et al. *Diabetes and Metabolism* 17:379–382 (1991) and Westhoff-Bleck et al. *Drug Safety* 6(1):28–36 (1991).

While lipidic contrast agents, such as Lipiodol (commercialized by Guerbet Laboratories), are less quickly diffused into the tissues, they form unstable emulsions of high viscosity. Further, the emulsions often form particle sizes of several microns, which can produce granulomas and provoke, in the case of an intravenous injection, fatty embolus. See *Dictionnaire Vidal*, p. 1562 (1992). Hepatic toxicity has also been observed for emulsions of lipidic iodinated products. See Mutzel et al. U.S. Pat. No. 4,367,216 and Wolf et al. U.S. Pat. No. 5,114,703. Accordingly, they can only be safely used in specific applications such as in lymphography or sialography.

Brominated perfluorocarbon contrast agents have also been used for contrast enhancement. For example, the Imagent product line from Alliance Pharmaceutical Corp. is based on brominated perfluorocarbon agents. These agents can be used in either the pure state or in the form of emulsions. Further, their intravenous persistence is longer than the hydrosoluble agents and they have reduced toxicity as compared to both the hydrosoluble and lipidic agents. See Long et al. *Blood Substitutes*, pp. 441–442 (Marcel Dekker Inc., N.Y. (1989)). However, their radiopaque constituent, perfluorooctyl bromide (Perflubron or PFOB), being bromine based, possesses reduced opacity under radiation as compared to that of iodine, for example. Therefore, higher doses are often necessary to achieve suitable contrast levels.

Iodinated perfluoroalkyated compounds have been studied for use as contrast enhancement agents. However, to date, most of these agents have proven too toxic for use in biomedical applications. See Long et al. in *Preparations, Properties and Industrial Applications of Organofluorine Compounds* p. 139, R. E. Banks, Ed. (Ellis Horword Ltd., Chichester, U.K., (1982)). They were essentially perfluoroalkylated compounds, iodinated at one of the chain termini. Compare, however, U.S. Pat. No. 4,367,216 to Mutzel et al., which discloses triiodinated 5-aminoisophthalic acid derivatives.

Accordingly, it would be beneficial to develop a contrast enhancement agent to improve upon the prior art and overcome and/or ameliorate some of the shortcomings presented thereby, such as high toxicity, limited persistence, and limited opacity.

SUMMARY OF THE INVENTION

The present invention solves and/or ameliorates many of the problems in the art by providing iodinated perfluoroalkyated compounds and compositions formed therefrom having superior opacity and limited toxicity. Encompassed in the invention are emulsions, microemulsions, dispersions, or gels of non-toxic iodinated fluorocarbon compounds. Also encompassed are compositions comprising such compounds for biomedical use. The compositions are particularly useful as contrast enhancement agents, principally in radiography and scintigraphy.

The compositions advantageously contain iodinated fluorocarbon molecules which are surprisingly inert and stable. They are sterilizable by heat without degradation or variation in the pH. Further, they are non-toxic after intravenous injection, and lend an opacity much stronger than that obtained with other perfluorinated contrast agents.

In accordance with the present invention there is provided a dispersion, emulsion, microemulsion, or gel, comprising:

an oily phase comprising an iodinated fluorinated compound possessing an iodine atom in an internal position in the molecular structure of the compound, provided that the compound is not terminally iodinated, an aqueous phase, and a surfactant.

In a preferred embodiment, the iodinated fluorocarbon compound is a iodinated fluorinated compound of the general formula:

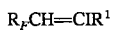

$$R_F\text{CH}=\text{CIR}^1$$

wherein $R_F$ is a fluorocarbon radical, which may be linear, branched, or cyclic, and which may be saturated or unsaturated, and is of 2 to 12 carbon atoms, in which 50 to 100% of the hydrogen atoms have been replaced by fluorine atoms, and wherein the fluorocarbon radical may comprise in its chain one or several oxygen, sulfur, chlorine and/or bromine atoms, and $R^1$ is either a fluorocarbon radical $R_F$I or a hydrocarbon radical $R_H$, wherein $R_F$ is a linear, branched, or cyclic, saturated or unsaturated, of 2 to 12 carbon atoms, in which 50 to 100% of the hydrogen atoms have been replaced by fluorine atoms, and wherein the fluorocarbon radical has at least 4 fluorine atoms and may bear in its chain one or several atoms of oxygen, sulfur, chlorine and/or bromine, and $R_H$ is a linear, branched, or cyclic, saturated or unsaturated, of 2 to 14 carbon atoms, and may bear in its chain one or several atoms of oxygen and/or sulfur.

The compounds used in the present invention are useful in biomedical applications and can be employed as either the native iodinated fluorine compound of the general structure, $R_F\text{CH}=\text{CIR}^1$, or as diluted in at least one appropriate organic compound such as fluorocarbon, or as an emulsion, microemulsion, dispersion or gel incorporating the iodinated fluorine compound, such as those described below. Similarly, the iodinated fluorinated compounds can be formulated in appropriate carriers or administration vehicles.

In a particularly preferred embodiment, the first fluorocarbon radical is selected from the group consisting of $F(CF_2)_i$— where i is an integer from 2 to 12, $(CF_3)_2CF$—

$(CF_2)_j$— where j is an integer from 0 to 8, and $CF_3$—$[CF_2CF(CF_3)]_k$— where k is an integer from 1 to 4, $C_2F_5$—$[CF_2CF(CF_3)]_k$— where k is an integer from 1 to 4, $(CF_3)_2CF$—$[CF_2CF(CF_3)]_k$— were k is an integer from 1 to 4, $(R_{F2})(R_{F3})CFO(CF_2$—$CF_2)L$ where $R_{F2}$ and $R_{F3}$ independently represent a moiety selected from the group consisting of $CF_3$—, $C_2F_5$—, n—$C_3F_7$—, and $CF_3CF_2CF(CF_3)$— where L is an integer from 1 to 6, $(R_{F2})(R_{F3})CFO(CF_2$—$CF_2)L$ where $R_{F2}$ and $R_{F3}$ together form —$(CF_2)_4$— or —$(CF_2)_5$— and where L is an integer from 1 to 6, $CF_3CF_2O[CF_2CF_2O]_mCF_2$— where m is an integer from 0 to 5, and $CF_3(CF_2)_2O([CF(CF_3)CF_2O]_n$—$CF(CF_3)$— where n is an integer from 0 to 6, the second fluorocarbon radical is selected from the group consisting of $F(CF_2)_i$— where i is an integer from 2 to 12, $(CF_3)_2CF$—$(CF_2)_j$— where j is an integer from 0 to 8, and $CF_3$—$[CF_2CF(CF_3)]_k$— where k is an integer from 1 to 4, $C_2F_5$—$[CF_2CF(CF_3)]_k$— where k is an integer from 1 to 4, $(CF_3)_2CF$—$[CF_2CF(CF_3)]_k$— where k is an integer from 1 to 4, $(R_{F2})(R_{F3})CFO(CF_2$—$CF_2)L$ where $R_{F2}$ and $R_{F3}$ independently represent a moiety selected from the group consisting of $CF_3$—, $C_2F_5$—, n—$C_3F_7$—, and $CF_3CF_2CF(CF_3)$— where L is an integer from 1 to 6, $(R_{F2})(R_{F3})CFO(CF_2$—$CF_2)L$ where $R_{F2}$ and $R_{F3}$ together form —$(CF_2)_4$— or —$(CF_2)_5$— and where L is an integer from 1 to 6, $CF_3CF_2O[CF_2CF_2O]_mCF_2$— where m is an integer from 0 to 5, and $CF_3(CF_2)_2O([CF(CF_3)CF_2O]_n$—$CF(CF_3)$— where n is an integer from 0 to 6, and the hydrocarbon radical is selected from the group consisting of $CH_3$—$(CH_2)_{y1}$— wherein $y_1$ is an integer between 1 and 15, $CH_3$—$(CH_2)_{y2}(CH=CH)_q(CH_2)_{y3}$ wherein y2 is an integer between 1 and 15, q=0 or 1, and y3 is an integer between 0 and 15, $CH_3(CH_2)_{y7}$ in which y7 is an integer between 1 and 11, $CH_3$—$(CH_2)_{y2}$—S—$(CH_2)_{y4}$— wherein y2 is an integer between 1 and 15 and y4 is an integer between 1 and 15, $CH_3$—$(CH_2$—$CH_2O)_{y5}$—$CH_2$— wherein y5 is an integer between 1 and 8, and $CH_3$—$(CH(CH_3)CH_2O)_{y6}$—$CH(CH_3)$— wherein y6 is an integer between 1 and 11. In a highly preferred embodiment, $R_F$ is $F(CF_2)_i$ in which i is an integer between 2 and 12 and $R^1$ is $CH_3(CH_2)_{y7}$ in which y7 is an integer between 1 and 11. In another highly preferred embodiment, oily phase comprises $C_6F_{13}$—$CH=C(I)$—$C_6H_{13}$ or $C_8F_{17}$—$CH=C(I)$—$C_8H_{17}$.

Compositions of the invention can also be formed into lipidic membranes, liposomes, or niosomes containing the iodinated fluorine compound. These may be prepared by classical procedures comprising the use of techniques by solvent, injection, ultrasounds or mechanical high pressure homogenizers may also be used.

In a preferred embodiment, the oily phase additionally comprises a fluorocarbon. Examples of preferred fluorocarbons includes perfluorodecaline, perfluorooctyl bromide, perfluorodecyl bromide, 1,2-bis-F-alkylethenes or any other appropriate perfluorocarbon or compound, whether highly fluorinated or not.

Various surfactants are useful in the present invention. For example, lecithins, polyoxyethylene-polyoxypropylene copolymers, sorbitan polyoxyethylenes, phospholipids such as egg-yolk, soya or synthetic lipids, perfluoroalkyl phospholipids and the other synthetic perfluoroalkyl surfactants are all effective as surfactants in the present invention.

As will be appreciated, additional constituents, additives, and the like, can be incorporated with the oily phase, aqueous phase, and/or the surfactant. In a preferred embodiment, for example, the aqueous phase can also comprise one or several other additives such as mineral salts, buffers, osmotic agents, oncotic agents, anti-oxidants such as alpha-tocopherol, pharmaceuticals, and nutritive products. Such additives, are chosen according to and depending upon the intended use of the composition.

In a preferred embodiment, the ratio of the oily phase, aqueous phase, and surfactant comprise from 10 to 120% weight/volume of the oily phase, from 0.1 to 10% weight/volume of the surfactant, and the aqueous phase forms the balance. Such composition can take the form of an emulsion, microemulsion, or gel.

In accordance with another aspect of the present invention, there is provided a composition for biomedical use comprising an iodinated fluorinated compound in a fluorocarbon carrier, wherein the compound has the following general structure

$$R_FCH=CIR^1$$

wherein, $R_F$ is a linear, branched, or cyclic first fluorocarbon radical, having 2 to 12 carbon atoms in which 50 to 100% of the hydrogen atoms have been replaced by fluorine atoms, and $R^1$ is selected from the group consisting of a second fluorocarbon radical and a hydrocarbon radical, wherein, the second fluorocarbon radical is linear, branched, or cyclic, having 2 to 12 carbon atoms in which 50 to 100% of the hydrogen atoms have been replaced by fluorine atoms, and the hydrocarbon radical is linear, branched, or cyclic, having 2 to 4 carbon atoms.

In a preferred embodiment, the first fluorocarbon radical is selected from the group consisting of $F(CF_2)_i$— where i is an integer from 2 to 12, $(CF_3)_2CF$—$(CF_2)_j$— where j is an integer from 0 to 8, and $CF_3$—$[CF_2CF(CF_3)]_k$— where k is an integer from 1 to 4, $C_2F_5$—$[CF_2CF(CF_3)]_k$— where k is an integer from 1 to 4, $(CF_3)_2CF$—$[CF_2CF(CF_3)]_k$— where k is an integer from 1 to 4, $(R_{F2})(R_{F3})CFO(CF_2$—$CF_2)L$ where $R_{F2}$ and $R_{F3}$ independently represent a moiety selected from the group consisting of $CF_3$—, $C_2F_5$—, n—$C_3F_7$—, and $CF_3CF_2CF(CF_3)$— where L is an integer from 1 to 6, $(R_{F2})(R_{F3})CFO(CF_2$—$CF_2)L$ where $R_{F2}$ and $R_{F3}$ together form —$(CF_2)_4$— or —$(CF_2)_5$— and where L is an integer from 1 to 6, $CF_3CF_2O[CF_2CF_2O]_mCF_2$— where m is an integer from 0 to 5, and $CF_3(CF_2)_2O([CF(CF_3)CF_2O]_n$—$CF(CF_3)$— where n is an integer from 0 to 6, the second fluorocarbon radical is selected from the group consisting of $F(CF_2)_i$— where i is an integer from 2 to 12, $(CF_3)_2CF$—$(CF_2)_j$— where j is an integer from 0 to 8, and $CF_3$—$[CF_2CF(CF_3)]_k$— where k is an integer from 1 to 4, $C_2F_5$—$[CF_2CF(CF_3)]_k$— where k is an integer from 1 to 4, $(CF_3)_2CF$—$[CF_2CF(CF_3)]_k$— where k is an integer from 1 to 4, $(R_{F2})(R_{F3})CFO(CF_2$—$CF_2)L$ where $R_{F2}$ and $R_{F3}$ independently represent a moiety selected from the group consisting of $CF_3$—, $C_2F_5$—, n—$C_3F_7$—, and $CF_3CF_2CF(CF_3)$— where L is an integer from 1 to 6, $(R_{F2})(R_{F3})CFO(CF_2$—$CF_2)L$ where $R_{F2}$ and $R_{F3}$ together form —$(CF_2)_4$— or —$(CF_2)_5$— and where L is an integer from 1 to 6, $CF_3CF_2O[CF_2CF_2O]_mCF_2$— where m is an integer from 0 to 5, and $CF_3(CF_2)_2O([CF(CF_3)CF_2O]_n$—$CF(CF_3)$— where n is an integer from 0 to 6, and the hydrocarbon radical is selected from the group consisting of $CH_3$—$(CH_2)_{y1}$— wherein $y_1$ is an integer between 1 and 15, $CH_3$—$(CH_2)_{y2}(CH=CH)_q(CH_2)_{y3}$ wherein y2 is an integer between 1 and 15, q=0 or 1, and y3 is an integer between 0 and 15, $CH_3(CH_2)_{y7}$ in which y7 is an integer between 1 and 11, $CH_3$—$(CH_2)_{y2}$—S—$(CH_2)_{y4}$— wherein y2 is an integer between 1 and 15 and y4 is an integer between 1 and 15, $CH_3$—$(CH_2$—$CH_2$—$O)_{y5}$—$CH_2$— wherein y5 is an integer between 1 and 8, and $CH_3$—$(CH(CH_3)CH_2O)_{y6}$—$CH(CH_3)$— wherein y6 is an integer between 1 and 11.

In a highly preferred embodiment, $R_F$ is $F(CF_2)_i$ in which i is an integer between 2 and 12 and $R^1$ is $CH_3(CH_2)_{y7}$ in which y7 is an integer between 1 and 11, for example, $C_6F_{13}$—CH=C(I)—$C_6H_{13}$ or $C_8F_{17}$—CH=C(I)—$C_8H_{17}$. The fluorocarbon carrier is preferably selected from the group consisting of perfluorodecalin, perfluorooctyl bromide, perfluorodecyl bromide and 1,2-bis-F-alkylethenes.

In accordance with another preferred embodiment of the invention, there is provided an emulsion, comprising an oily phase comprising up to 120% weight/volume of an iodinated fluorinated compound of the following general structure $$R_F\text{CH}=\text{CIR}^1$$

wherein, $R_F$ is a linear, branched, or cyclic first fluorocarbon radical having 2 to 12 carbon atoms selected from the group consisting of $F(CF_2)_i$— where i is an integer from 2 to 12, $(CF_3)_2CF$—$(CF_2)_j$— where j is an integer from 0 to 8, and $CF_3$—$[CF_2CF(CF_3)]_k$— where k is an integer from 1 to 4, $C_2F_5$—$[CF_2CF(CF_3)]_k$— where k is an integer from 1 to 4, $(CF_3)_2CF$—$[CF_2CF(CF_3)]_k$— where k is an integer from 1 to 4, $(R_{F2})(R_{F3})CFO(CF_2$—$CF_2)L$ where $R_{F2}$ and $R_{F3}$ independently represent a moiety selected from the group consisting of $CF_3$—, $C_2F_5$—, n—$C_3F_7$—, and $CF_3CF_2CF(CF_3)$— where L is an integer from 1 to 6, $(R_{F2})(R_{F3})CFO(CF_2$—$CF_2)L$ where $R_{F2}$ and $R_{F3}$ together form —$(CF_2)_4$— or —$(CF_2)_5$— and where L is an integer from 1 to 6, $CF_3CF_2O[CF_2CF_2O]_mCF_2$— where m is an integer from 0 to 5, and $CF_3(CF_2)_2O([CF(CF_3)CF_2O]_n$—$CF(CF_3)$— where n is an integer from 0 to 6, $R^1$ is selected from the group consisting of a linear, branched, or cyclic second fluorocarbon radical having 2 to 12 carbon atoms and a linear, branched, or cyclic hydrocarbon radical having 2 to 14 carbon atoms, wherein, the second fluorocarbon radical is selected from the group consisting of $F(CF_2)_i$— where i is an integer from 2 to 12, $(CF_3)_2CF$—$(CF_2)_j$— where j is an integer from 0 to 8, and $CF_3$—$[CF_2CF(CF_3)]_k$— where k is an integer from 1 to 4, $C_2F_5$—$[CF_2CF(CF_3)]_k$— where k is an integer from 1 to 4, $(CF_3)_2CF$—$[CF_2CF(CF_3)]_k$— where k is an integer from 1 to 4, $(R_{F2})(R_{F3})CFO(CF_2$—$CF_2)L$ where $R_{F2}$ and $R_{F3}$ independently represent a moiety selected from the group consisting of $CF_3$—, $C_2F_5$—, n—$C_3F_7$—, and $CF_3CF_2CF(CF_3)$— where L is an integer from 1 to 6, $(R_{F2})(R_{F3})CFO(CF_2$—$CF_2)L$ where $R_{F2}$ and $R_{F3}$ together form —$(CF_2)_4$— or —$(CF_2)_5$— and where L is an integer from 1 to 6, $CF_3CF_2O[CF_2O]_mCF_2$— where m is an integer from 0 to 5, and $CF_3(CF_2)_2O([CF(CF_3)CF_2O]_n$—$CF(CF_3)$— where n is an integer from 0 to 6, and the hydrocarbon radical is selected from the group consisting of $CH_3$—$(CH_2)_{y1}$— wherein $y_1$ is an integer between 1 and 15, $CH_3$—$(CH_2)_{y2}(CH=CH)_q(CH_2)_{y3}$ wherein y2 is an integer between 1 and 15, q=0 or 1, and y3 is an integer between 0 and 15, $CH_3(CH_2)_{y7}$ in which y7 is an integer between 1 and 11, $CH_3$—$(CH_2)_{y2}$—S—$(CH_2)_{y4}$— wherein y2 is an integer between 1 and 15 and y4 is an integer between 1 and 15, $CH_3$—$(CH_2$—$CH_2O)_{y5}$—$CH_2$— wherein y5 is an integer between 1 and 8, and $CH_3$—$(CH(CH_3)CH_2O)_{y6}$—$CH(CH_3)$— wherein y6 is an integer between 1 and 11, an essentially aqueous phase, and a surfactant.

In a preferred embodiment, $R_F$ is $F(CF_2)_i$ in which i is an integer between 2 and 12 and $R^1$ is $CH_3(CH_2)_{y7}$ in which y7 is an integer between 1 and 11, such as $C_6F_{13}$—CH=C(I)—$C_6H_{13}$ or $C_8F_{17}$—CH=C(I)—$C_8H_{17}$. The surfactant is preferably selected from the group consisting of copolymers of polyoxyethylene-polyoxypropylene, sorbitan polyoxyethylenes, and perfluorinated surfactants, and more preferably, lecithin.

The aqueous phase may additionally comprise one or more additives. In preferred embodiments, the additive is selected from the group consisting of mineral salts, buffers, osmotic or oncotic agents, pharmaceuticals, nutritive products, and anti-oxidants.

In accordance with another embodiment of the invention, there is provided a contrast agent for use in radiography comprising any one of the aforementioned compositions. Alternatively, a contrast agent for use in scintigraphy may be prepared, wherein the iodine atom in one of the foregoing compositions is a radioactive iodine atom selected from the group consisting of iodine-123, iodine-125, and iodine-131.

In accordance with another preferred embodiment of the invention, there is provided a method for performing a radiographic procedure, comprising administering a radiographic contrast enhancement effective amount of an iodinated fluorinated compound to a patient, wherein the compound has the following general structure $$R_F\text{CH}=\text{CIR}^1$$

wherein, $R_F$ is a linear, branched, or cyclic first fluorocarbon radical, having 2 to 12 carbon atoms in which 50 to 100% of the hydrogen atoms have been replaced by fluorine atoms, and $R^1$ is selected from the group consisting of a second fluorocarbon radical and a hydrocarbon radical, wherein, the second fluorocarbon radical is linear, branched, or cyclic, having 2 to 12 carbon atoms in which 50 to 100% of the hydrogen atoms have been replaced by fluorine atoms, and the hydrocarbon radical is linear, branched, or cyclic, having 2 to 14 carbon atoms.

In a preferred embodiment, the first fluorocarbon radical is selected from the group consisting of $F(CF_2)_i$— where i is an integer from 2 to 12, $(CF_3)_2CF$—$(CF_2)_j$— where j is an integer from 0 to 8, and $CF_3$—$[CF_2CF(CF_3)]_k$— where k is an integer from 1 to 4, $C_2F_5$—$[CF_2CF(CF_3)]_k$— where k is an integer from 1 to 4, $(CF_3)_2CF$—$[CF_2CF(CF_3)]_k$— where k is an integer from 1 to 4, $(R_{F2})(R_{F3})CFO(CF_2$—$CF_2)L$ where $R_{F2}$ and $R_{F3}$ independently represent a moiety selected from the group consisting of $CF_3$—, $C_2F_5$—, n—$C_3F_7$—, and $CF_3CF_2CF(CF_3)$— where L is an integer from 1 to 6, $(RF_{F2})(R_{F3})CFO(CF_2$—$CF_2)L$ where $R_{F2}$ and $R_{F3}$ together form —$(CF_2)_4$— or —$(CF_2)_5$— and where L is an integer from 1 to 6, $CF_3CF_2O[CF_2CF_2O]_mCF_2$— where m is an integer from 0 to 5, and $CF_3(CF_2)_2O([CF(CF_3)CF_2O]_n$—$CF(CF_3)$— where n is an integer from 0 to 6, the second fluorocarbon radical is selected from the group consisting of $F(CF_2)_i$— where i is an integer from 2 to 12, $(CF_3)_2CF$—$(CF_2)_j$— where j is an integer from 0 to 8, and $CF_3$—$[CF_2CF(CF_3)]_k$— where k is an integer from 1 to 4, $C_2F_5$—$[CF_2CF(CF_3)]_k$— where k is an integer from 1 to 4, $(CF_3)_2CF$—$[CF_2CF(CF_3)]_k$— where k is an integer from 1 to 4, $(R_{F2})(R_{F3})CFO(CF_2$—CF)L where $R_{F2}$ and $R_{F3}$ independently represent a moiety selected from the group consisting of $CF_3$—, $C_2F_5$—, n—$C_3F_7$—, and $CF_3CF_2CF(CF_3)$— where L is an integer from 1 to 6, $(R_{F2})(R_{F3})CFO(CF_2$—$CF_2)L$ where $R_{F2}$ and $R_{F3}$ together form —$(CF_2)_4$— or —$(CF_2)_5$— and where L is an integer from 1 to 6, $CF_3CF_2O[CF_2CF_2O]_mCF_2$— where m is an integer from 0 to 5, and $CF_3(CF_2)_2O([CF(CF_3)CF_2O]_n$—$CF(CF_3)$— where n is an integer from 0 to 6, and the hydrocarbon radical is selected from the group consisting of $CH_3$—$(CH_2)_{y1}$— wherein $y_1$ is an integer between 1 and 15, $CH_3$—$(CH_2)_{y2}(CH=CH)_q(CH_2)_{y3}$ wherein y2 is an integer between 1 and 15, q=0 or 1, and y3 is an integer between 0 and 15, $CH_3(CH_2)_{y7}$ in which y7 is an integer between 1 and 11, $CH_3$—$(CH_2)_{y2}$—S—$(CH_2)_{y4}$— wherein y2 is an integer between 1 and 15 and y4 is an integer between 1 and 15, $CH_3$—$(CH_2$—$CH_2$—$O)_{y5}$—$CH_2$— wherein y5 is an integer between 1 and 8, and $CH_3$—$(CH(CH_3)CH_2O)_{y6}$—$CH(CH_3)$— wherein y6 is an integer between 1 and 11.

In a preferred embodiment, $R_F$ is $F(CF_2)_i$ in which i is an integer between 2 and 12 and $R^1$ is $CH_3(CH_2)_{y7}$ in which y7 is an integer between 1 and 11, such as $C_6F_{13}$—CH=C(I)—$C_6H_{13}$, or $C_8F_{17}$—CH=C(I)—$C_8H_{17}$.

BRIEF DESCRIPTION OF THE DRAWING FIGURES

DETAILED DESCRIPTION OF THE PREFERRED EMBODIMENTS

Figure 1:
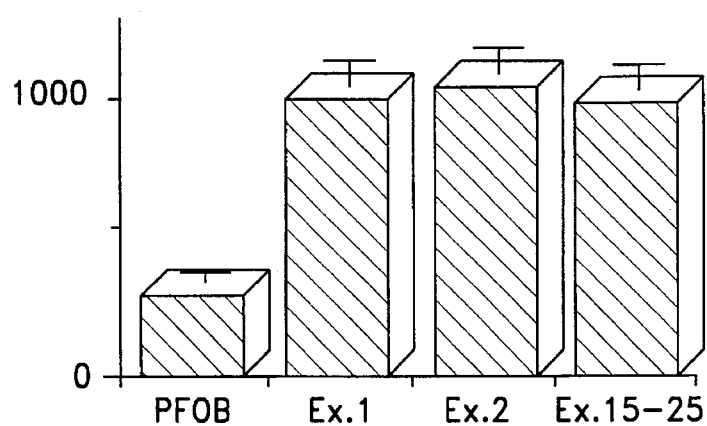
FIG. 1 is a bar graph showing comparative radiopacity from an in vitro study of an iodinated fluorinated compound used in the present invention and a recent conventional radiopaque fluorocarbon, perfluorooctyl bromide (PFOB).

The present invention relates to emulsions, microemulsions, gels and other vehicles incorporating iodinated fluorinated compounds that are not terminally iodinated. Such compositions demonstrate enhanced stability and radiopacity with highly reduced toxicity. The invention also relates to the biomedical use of the compounds of the present invention, particularly for use a radiopaque contrast enhancement agents.

In a preferred embodiment, the invention provides compositions for biomedical uses, notably for diagnosis, comprising at least one iodinated fluorine compound possessing an iodine atom inside the molecular structure and not at one end. This iodinated fluorine compound is preferably of the following general formula:

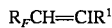

wherein $R_F$ is a linear, branched, or cyclic first fluorocarbon radical, having 2 to 12 carbon atoms in which 50 and 100% of the hydrogen atoms have been replaced by fluorine atoms, the first fluorocarbon radical having at least 4 fluorine atoms; and $R^1$ is selected from the group consisting of a second fluorocarbon radical and a hydrocarbon radical, wherein, the second fluorocarbon radical is linear, branched, or cyclic, having 2 to 12 carbon atoms in which 50 to 100% of the hydrogen atoms have been replaced by fluorine atoms, the second fluorocarbon radical having at least 4 fluorine atoms; and the hydrocarbon radical is linear, branched, or cyclic, having 2 to 14 carbon atoms.

The compositions of the invention may be constituted by the pure iodinated fluorine compound $R_FCH=CIR^1$, by the iodinated fluorine compound diluted in at least one appropriate organic compound such as a fluorocarbon, or by an emulsion, microemulsion, dispersion or gel incorporating the iodinated fluorine compound, such as described above.

In conformity with the invention, compositions in the form of lipidic membranes, liposomes or niosomes containing the iodinated fluorine compound, prepared by classical or conventional techniques, such as solvent injection, ultrasound, and/or mechanical high-pressure homogenization may also be used.

Examples of the preferred fluorocarbon radicals, $R_F$ and $R_F$, (when $R^1$ is a fluorocarbon radical), for use in the present invention include the following:

a) $F(CF_2)_i$— where i is an integer from 2 to 12;
b) $(CF_3)_2CF$—$(CF_2)_j$— where j is an integer from 0 to 8;
c) $R_{F1}[CF_2CF(CF_3)]_k$— where $R_{F1}$ represents $CF_3$—, $C_2F_5$—, or $(CF_3)_2CF$— and k is an integer from 1 to 4;
d) $(R_{F2})(R_{F3})CFO(CF_2$—$CF_2)L$ where $R_{F2}$ and $R_{F3}$ independently represent $CF_3$—, $C_2F_5$—, n—$C_3F_7$— or $CF_3CF_2CF(CF_3)$— or $R_{F2}$ and $RF_3$ together form —$(CF_2)_4$— or —$(CF_2)_5$—, and L is an integer from 1 to 6;
e) $CF_3CF_2O[CF_2CF_2O]_mCF_2$— where m is an integer from 0 to 5, and
f) $CF_3(CF_2)_2O([CF(CF_3)CF_2O]_n$—$CF(CF_3)$— where n is an integer from 0 to 6.

Examples of the preferred hydrocarbon radicals for use in the invention, when $R^1$ is $R_H$, include the following:

a) $CH_3$—$(CH_2)_{y1}$— wherein $y_1$ is an integer between 1 and 15;
b) $CH_3$—$(CH_2)_{y2}(CH=CH)_q(CH_2)_{y3}$ wherein y2 is an integer between 1 and 15, q=0 or 1, and y3 is an integer between 0 and 15;
c) $CH_3$—$(CH_2)_{y2}$—S—$(CH_2)_{y4}$— wherein y2 is an integer between 1 and 15 and y4 is an integer between 1 and 15;
d) $CH_3$—$(CH_2$—$CH_2$—$O)_{y5}$—$CH_2$— wherein y5 is an integer between 1 and 8; and
e) $CH_3$—$(CH(CH_3)CH_2O)_{y6}$—$CH(CH_3)$— wherein y6 is an integer between 1 and 11.

Highly preferred iodinated fluorinated compounds of the present invention include compounds of the general structure:

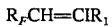

wherein $R_F$ is $F(CF_2)_{i1}$, wherein i1 is an integer between 2 and 12 and $R_1$ is a hydrocarbon radical having the formula $CH_3(CH_2)_{y7}$, wherein y7 is an integer between 1 and 11. Also highly preferred are compounds in which $R_F$ is $F(CF_2)_{i1}$, wherein i1 is an integer between 2 and 9, and $R^1$ is a fluorocarbon radical having the formula $F(CF_2)_{i2}$, wherein i2 is an integer between 2 and 9.

The iodinated fluorinated compounds of the present invention can be prepared by conventional techniques. Typically an alkyne of the general structure $CH=CHR^1$ is reacted with a terminally iodinated fluorinated compound of the general structure $R_FI$ with an appropriate catalyst to obtain the compounds used in the present invention. A more detailed discussion of the synthesis of the compounds of the present invention is provided in the following references: Knell, U.S. Pat. No. 4,058,573, Ojima, European Patent Application No. 0 115 943, Chen et al. *J. Fluorine Chem.* 36:149–161 (1987), Ishihara et al. *Chem. Let.* 1895–1896 (1986), and Brace *J. Fluorine Chem.* 20:313–327 (1982), the disclosures of each of which are hereby incorporated by reference.

As will be appreciated, the reactions typically produce both cis and trans isomers of the compounds of the present invention, each of which appear to function with identical efficacy and safety in the present invention. Therefore, the invention includes mixtures of the isomers as well as either of the cis or trans isomer as separated.

The compounds of the present invention are particularly useful as contrast agents in radiography, especially in lymphography. For example, the superior radiopacity of the compounds of the present invention is demonstrated in FIG. 1, which is a bar graph showing the comparative radiopacity (in Hounsfield units) from an in vitro study between three iodinated fluorinated compounds of the present invention (right) and a recent conventional radiopaque fluorocarbon, perfluorooctyl bromide ("PFOB") (left).

The compounds of the present invention are also useful in scintigraphy. However, in scintigraphy, a radioactive isotope of iodine is used for the iodine moiety. Preferred iodine isotopes for use in scintigraphy are iodine-123, iodine-125 and iodine-131, preferably, however, iodine-123 or iodine-131 are used. The radioactive iodinated fluorinated compounds of the present invention can be prepared through similar processes as the nonradioactive compounds of the invention, as described above.

In addition to their remarkable radiopacity, the compounds used in the present invention showed surprising stability. For example, when stored at room temperature, in darkness, the compounds did not show any visible nor structural degradations for periods as long as fifteen (15) years.

Beyond radiopacity and stability, the compounds used in the present invention are biocompatible. They are tolerated in high doses in animals. For example, in intraperitoneal administration in mice, the mice were still alive at the end of the protocol, one month post injection, even after doses of up to 45 g/kg of the iodinated fluorinated compounds used in the present invention had been injected. Further, in intravenous administration to mice of the compounds used in the present invention in emulsified form, the mice lived past the end of the protocol, one month post injection of doses up to 8 g/kg.

While not wishing to be bound to a particular theory, we believe that a primary reason for the low levels of toxicity observed for the compounds of the present invention is due to the placement of the iodine moiety on the internal structure of the molecule, as compared to terminal substitution as was used in many prior art compositions. Further, it is possible that the placement of the iodine moiety at the carbon-carbon double bond acts to reduce toxicity further, i.e., through reducing the lability and/or reactivity of the iodine.

The compounds used in the present invention are also rapidly excreted. For example, the half-life of a typical emulsion (example 3) in the liver of rats after injection is less than 10 days, as determined by fluorine NMR.

The compounds used in the present invention can be administered intraperitoneally in their neat form or as diluted in a fluorocarbon compound or in another suitable carrier or vehicle. For intravenous administration or administration into other bodily cavities or organs, however, inclusion of the compounds of the present invention in an emulsion, microemulsion, dispersion, or gel is preferred.

Except as otherwise provided or as required by context, the term "emulsion" shall include microemulsions, dispersions, and gels. Emulsions can be prepared by conventional techniques. Typically, one or more surfactant(s) are dispersed in an aqueous phase, which may contain other additives. Thereafter, the compounds of the present invention are provided as, or as a part of, an oily phase which is added to the aqueous phase, followed by dispersion of the whole utilizing conventional techniques.

As mentioned, the aqueous phase can also include one or more additives to achieve certain, desired effects, such as particle size stability, osmolarity, thermal stability, and the like. Therefore, additives such as mineral salts, buffers, osmotic agents, oncotic agents, anti-oxidants such as alpha-tocopherol, and pharmaceutical and/or nutritive products, chosen according to the application of the emulsion are contemplated, as well as other agents.

A variety of surfactants are useful in accordance with the present invention. Like additives in the aqueous phase, surfactants are chosen according to the desired properties of the emulsion. Examples of suitable surfactants for use in the present invention include lecithins, polyoxyethylene-polyoxypropylene copolymers, sorbitan polyoxy-ethylenes, phospholipids such as egg-yolk, soya or synthetic lipids, perfluoroalkyl phospholipids and the other synthetic perfluoroalkyl surfactants.

Also in the emulsions, the oily phase may additionally comprise other components. For example, it is often desirable to include a fluorocarbon, such as perfluorodecalin, perfluorooctyl bromide, perfluorodecyl bromide, 1,2-bis-F-alkylethenes, or other appropriate perfluorocarbons. Similarly, as will be understood, other lipophilic compounds, whether highly fluorinated or not, may also be included in the oily phase.

The preferred ratios of the components utilized to form the emulsions or gels in accordance with the present invention are generally as follows:

from 10 to 120% in weight/volume of an oily phase, from 0.1 to 10% in weight/volume of surfactant(s), and the aqueous phase making up the balance.

Microemulsions are preferably prepared with the following ratios:

from 10 to 120% in weight/volume of an oily phase, from 3 to 30% in weight/volume of surfactant(s), and the aqueous phase making up the balance.

As was mentioned above, these compositions may additionally comprise a fluorocarbon.

Upon providing, mixing, and dispersing the selected constituents of the emulsion, an emulsion is formed through appropriate agitation, typically through high shear mixing.

Inclusion of the compounds of the present invention in liposome and other delivery constructs or vehicle is also contemplated, so long as the delivery construct or vehicle allows appropriate administration to the animal tissue in need of diagnosis or therapy. Delivery forms ranging from oral to intravenous or by injection into cavities or organs of the human or animal body, for the purpose of diagnosis or therapy, are also contemplated.

The compositions of the present invention are capable of sterilization through the use of heat or through other classical techniques, such as filtration.

Figure 2:
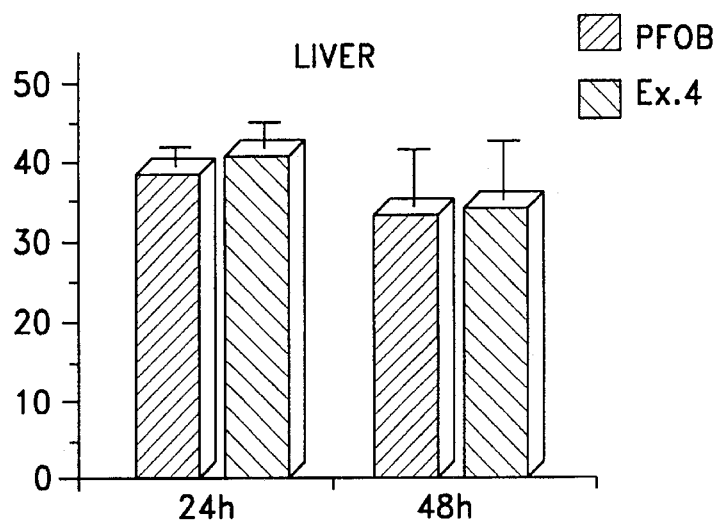
FIG. 2 is a bar graph showing comparative radiopacity, from an in vivo study in the liver of rabbits 24 and 48 hours post injection, between an emulsion including an iodinated fluorinated compound of the present invention and a PFOB emulsion prepared in accordance with the prior art.
Figure 3:
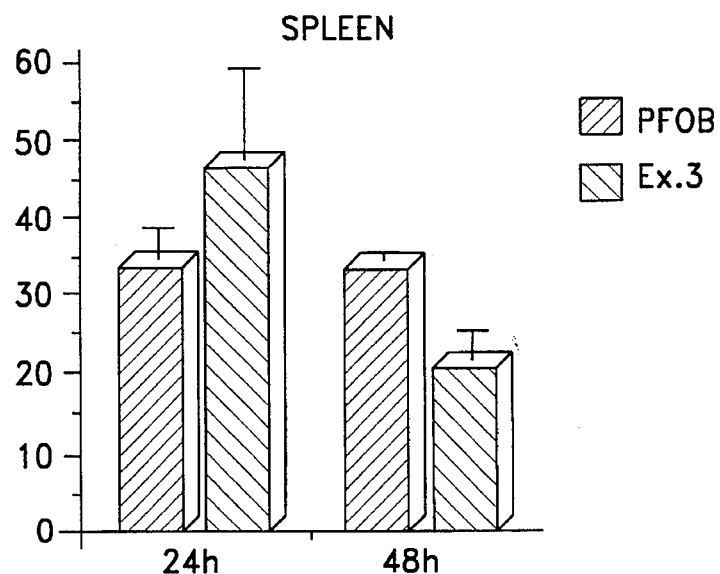
FIG. 3 is a bar graph showing comparative radiopacity, from an in vivo study in the spleen of rabbits 24 and 48 hours post injection, between an emulsion including an iodinated fluorinated compound of the present invention and a PFOB emulsion prepared in accordance with the prior art.

Other objects, characteristics, and advantages of the present invention will be more clearly seen on reading the following description of examples, which are of course illustrative, not limiting, and with reference to annexed FIGS. 1 to 3.

EXAMPLE 1

Radiopacity Of The Compound Of The Formula
$C_6F_{13}$—CH=CI—$C_6H_{13}$ (Compound IA)

In order to determine the relative radiopacity of the compounds used in the present invention to X-rays, we undertook an in vitro study to compare the radiopacity of the above compound (IA) in relation to the radiopacity of perfluorooctyl bromide.

A solution of Compound IA was prepared having a concentration of 0.34 mol/L in hexane. A second solution of perfluorooctyl bromide (PFOB) with the same concentration in hexane was also prepared. The opacity to X-rays of the respective compounds in the hexane solutions was determined using a Philips Tomoscan LX 120 kV, 175 mA apparatus.

The results of the experiment are shown in FIG. 1 which is a bar graph showing the relative radiopacity of Compound IA (lane 2) and PFOB (lane 1). As will be observed, Compound IA has approximately four times the radiopacity of PFOB.

EXAMPLE 2

Toxicity Of The Compound Of The Formula
$C_6F_{13}$—CH=CI—$C_6H_{13}$ (Compound IA)

In order to determine the toxicity of Compound IA, we injected mice intraperitoneally with the compound. In the experiment, 10 mice were interperitoneally injected with a dose of about 45 g/kg per animal of Compound IA. One month after the injection, all animals survived and were thriving, showing no ill effects.

Thus, Compound IA is tolerated at high doses by animals.

EXAMPLE 3

Radiopacity And Toxicity Of The Compounds Of
The Formula $C_8F_{17}$—CH=CI—$C_6H_{13}$ (Compound IIIA)

Following the procedure described in Example 1, we also measured the opacity to X-rays of Compound IIIA. As described, a solution of Compound IIIA was prepared at a concentration of 0.34 mol/L in hexane.

The results obtained are also shown in FIG. 1 (lane 3). A similar opacity was observed for Compound IIIA as was observed for Compound IA. Therefore, the opacity of the iodinated fluorinated compounds used in the invention appear to have opacities of about 4 times that of PFOB.

Compound IIIA was also tested for toxicity, following the procedure described in Example 2. A similar tolerance of greater than 45 g/kg animal weight was observed.

EXAMPLE 4

Preparation Of A Diluted Emulsion Comprising
Compound IA

An emulsion including Compound IA was prepared in accordance with the following Table:

TABLE I

| Component | Amount (wt/vol) |
| --- | --- |
| Compound IA | 34 |
| Lecithin | 6 |
| NaCl | 0.88 |
| EDTA $Na_2$, $2H_2O$ | 0.06 |
| $NaH_2PO_4$-$2H_2O$ | 0.192 |
| $Na_2HPO_4$-$12H_2O$ | 1.488 |
| α-Tocopherol | 0.006 |
| $H_2O$ (injectable) | QSP 100 ml |
| pH (adjusted w/1N NaOH) | 7.48 |

6 g of egg-yolk lecithin (Lipoid), which acts as surfactant, and a mixture of salts in conformity with table 1 were dispersed with the Ultra Turrax under nitrogen (8000 rpm, 1 min) in a phosphate buffer.

To this dispersion was added, under argon, 34 g of compound IA at the rate of 20 mL/min. The mixture was then dispersed over 10 min at 24000 rpm at a temperature of 30°–40° C.

The preemulsion obtained was transferred under argon into a microfluidizer (Microfluidics M110). After 12 passes under a pressure of 12000 psi in the chambers, the mixture was cooled to 30° C., the emulsion was recovered, and put into 20 mL flasks which were sterilized in an autoclave at 121° C. over 15 min.

The average particle size and particle distribution of the emulsion were measured by photosedimentation (±10%, HORIBA CAPA 700). The particle sizes over time are shown in the following Table:

TABLE II

| Time | Particle Size |
| --- | --- |
| After Sterilization | 0.20 |
| Day 30 | 0.21 |
| Day 60 | 0.19 |
| Day 90 | 0.23 |

The average particle size was 0.20 μm after sterilization. Moreover, the pH of the emulsion did not change during sterilization.

EXAMPLE 5

Preparation Of A Concentrated Emulsion Of
Compound IA

A more concentrated emulsion of Compound IA was prepared in accordance with the following Table:

TABLE III

| Component | Amount (wt/vol) |
| --- | --- |
| PFOB | — |
| Compound IA | 77 |
| Lecithin | 4 |
| NaCl | 0.55 |
| EDTA $Na_2$, $2H_2O$ | 0.039 |
| $NaH_2PO_4$-$2H_2O$ | 0.12 |
| $Na_2HPO_4$-$12H_2O$ | 0.93 |
| α-Tocopherol | 0.004 |
| $H_2O$ (injectable) | QSP 100 ml |
| pH (adjusted w/1N NaOH) | 7.48 |

The same procedure as in Example 4 was followed to prepare this emulsion. A stable emulsion of average particle size 0.39 μm was obtained.

EXAMPLE 6

Preparation Of Emulsions Of Mixtures Of
Compound IA and PFOB (Perfluorooctyl Bromide, Perflubron)

The same procedure was followed as in Example 4 to prepare emulsions with Compound IA and PFOB. A PFOB control emulsion was also prepared. The compositions of each of these emulsions are provided in the following Table:

TABLE IV

| Component | EX6A Amount (wt/vol) | EX6B Amount (wt/vol) | EX6C Amount (wt/vol) | Control Amount (wt/vol) |
|---|---|---|---|---|
| PFOB | 87 | 80 | 70 | 90 |
| Compound IA | 3 | 10 | 20 | — |
| Lecithin | 4 | 4 | 4 | 4 |
| NaCl | 0.55 | 0.55 | 0.55 | 0.55 |
| EDTA $Na_2$, $2H_2O$ | 0.039 | 0.039 | 0.039 | 0.039 |
| $NaH_2PO_4$-$2H_2O$ | 0.12 | 0.12 | 0.12 | 0.12 |
| $Na_2HPO_4$-$12H_2O$ | 0.93 | 0.93 | 0.93 | 0.93 |
| α-Tocopherol | 0.004 | 0.004 | 0.004 | 0.004 |
| $H_2O$ (injectable) | QSP 100 ml | QSP 100 ml | QSP 100 ml | QSP 100 ml |
| pH (adjusted w/1N NaOH) | 7.28 | 7.48 | 7.48 | 7.39 |

In these emulsions, the oily phase, which included the iodinated fluorinated compound of the invention mixed with perfluorooctyl bromide, corresponds to a 90% (w/v) perfluorocarbon emulsion. In preparing the emulsions, the iodinated fluorinated compound, Compound IA, was added first, then the perfluorooctyl bromide (Perflubron) was added.

The procedure discussed in Example 4 was followed to prepare the control emulsion. The control emulsion consisted of 90 g PFOB (as the oily phase) per 100 ml of the aqueous phase.

EXAMPLE 7

In Vitro Radiopacity Of An Emulsion Containing Compound IA

The opacity of the emulsions to X-rays was determined in vitro, as described in Examples 1 and 3. The opacity of the emulsion was observed to increase significantly as the concentration of the iodinated fluorinated compound increased. Thus, the opacity of the emulsion of EX6C was greater than the emulsion of EX6B, which was greater than the emulsion of EX6A, which was greater than the Control.

Surprisingly, the opacity to X-rays of the PFOB emulsion was substantially reduced relative to even EX6A, which contained only 3% (w/v) of Compound IA.

EXAMPLE 8

Comparison Of Emulsion Stability

The stability of the emulsion of Example 4 and that of the control emulsion in Example 6 were determined and compared over time for 90 days, at 40° C. The results obtained are provided in the following Table.

TABLE V

| Time | Compound IA Emulsion Particle Size | PFOB Emulsion Particle Size |
|---|---|---|
| After Sterilization | 0.20 | 0.12 |
| Day 30 | 0.21 | 0.17 |
| Day 60 | 0.19 | 0.22 |
| Day 90 | 0.23 | 0.25 |

In this table, the emulsions of the invention containing the iodinated fluorinated compounds alone appear to possess a comparable stability to the PFOB emulsion. This indicates that the emulsions of the invention have particle size stabilities in substantial conformity to prior art emulsions.

EXAMPLE 9

Intravenous Toleration Of Iodinated Perfluorinated Compound Emulsions

In this example, rats were tested for intravenous toleration of the emulsions incorporating the iodinated perfluorinated compounds of the invention conforming to the invention. Ten rats were injected intravenously with the emulsion of Example 5 containing 77% w/v of Compound IA at a 10 mL/kg body weight dose, which corresponds to 8 g/kg body weight of Compound IA.

After 30 days of observation, 100% of survival was noted.

EXAMPLE 10

Intravenous Toleration Of Iodinated Perfluorinated Compound Emulsions

In this example, the tolerability of the emulsions of the invention in mice was measured.

Ten mice were intravenously injected with the emulsion of Example 4 containing 34% w/v of Compound IA at a dose of 25 mL/kg, which corresponds to 8 g of Compound IA per kg body weight.

After 30 days' observation, 100% of the mice survived.

EXAMPLE 11

In Vivo Use Of The Iodinated Perfluorinated Compound Emulsions As Contrast Agents (Rabbit Liver Imaging)

In order to determine the ability of the compositions of the present invention to operate as effective contrast enhancement agents, we undertook an in vivo study in rabbits to image their livers.

In the study, 3 rabbits were injected with the emulsion of Example 5 at a dose of 3 mL of emulsion per kg of animal, i.e., 2.34 g/kg (4.2 mM of Compound IA), at the rate of 0.5 mL/min.

The radiopacity of the liver and spleen of each rabbit was then measured. The animals were held in a cage and radiopacity was measured using a Philips Tomoscan LX scanner at 120 kV and 175 mA, with continuous 5 mm scans slice with 7 mm intervals. The duration of each scan was 1.2 seconds. These measurements were taken before the injection, then at 24 hours, 48 hours, 7 days, 15 days, and 30 days after the injection.

The results from this study are shown in FIG. 2, which is a bar graph showing the comparison between the radiopacity of the liver (as determined by the increase in Hounsfield units) observed with the emulsion of Example 5 and a PFOB emulsion (Example 6), at 24 hours and 48 hours after injection. The concentration of the emulsion of Example 5 was at a dose of 0.30 g of Compound IA/kg (0.7 mM/kg). The concentration of the PFOB emulsion was at a dose of 2.7 g/kg body weight (5.4 mM of Perflubron/kg).

The results show that a comparable or higher contrast in the liver is obtained with the compositions of the present invention. Intriguingly, significantly lower concentrations of the compositions of the invention were necessary to obtain similar contrast enhancement to PFOB. For example, only 0.39 g of Compound IA was necessary to obtain equivalent contrast enhancement as 7 times as much Perflubron.

It is seen that better results are obtained with the emulsion of example 4 than with that of example 1 used at the same dose.

EXAMPLE 13

In Vivo Use Of The Iodinated Perfluorinated Compound Emulsions As Contrast Agents (Rabbit Spleen Imaging)

In this example, the contrast enhancement in rabbit spleens of the compositions of the present invention compared to a PFOB emulsion was measured. The emulsion of Example 4 was tested using the same conditions as those discussed in Example 12.

The results obtained are shown in FIG. 3, which is a bar graph, like that of FIG. 2, showing the comparison between the radiopacity of the spleen observed with the emulsion of Example 4 and a PFOB emulsion (Example 6), at 24 hours and 48 hours after injection. In the experiment, 1.5 mL/kg (0.5 g/kg, i.e. 1.79 mM/kg of Compound IA) of the emulsion of Example 4 and 3 mL/kg (2.7 g/kg, i.e. 5.4 mM/kg of Perflubron) (Example 6) were injected and the rabbits scanned as discussed in Example 12.

FIG. 3 demonstrates that the contrast power of the compositions of the present invention are much higher than that of the Perflubron emulsion, as practically the same contrast is obtained with much lower doses.

EXAMPLE 14

Effects Of Intravenous Injection Of The Compositions Of The Invention On Hepatic Function In Vivo In this example the effect of intravenous injection of the preparations of the invention on the hepatic function was tested. In this study, 3 rabbits were injected with the emulsified iodinated fluorinated compound of Example 4 at a dose of 3 mL/kg animal (1 g, i.e. 1.79 mM of Compound IA per kg of animal). Hematologic analysis at 24 hours, 48 hours, and 7 days after injection showed that the amount of bilirubin, alkaline phosphatase, and gamma GT were comparable to those of 3 control rabbits. These results indicate that the hepatic function was normal even when the liver remained highly charged with a contrast agent of the invention at 24 hours and 48 hours.

EXAMPLE 15

In Vitro Radiopacity And In Vivo Tolerance Of Compounds Used In The Present Invention In this experiment, we prepared and tested the following compositions of the present invention for in vitro radiopacity and in vivo tolerance in animals:

$C_4F_9$—CH=C(I)—$C_4F_9$ $C_4F_9$—CH=C(I)—$C_6F_{13}$ $C_6F_{13}$—CH=C(I)—$C_4F_9$ $C_2F_5$—CH=C(I)—$C_6F_{13}$ $C_2F_5$—CH=C(I)—$C_8F_{17}$ $C_6F_{13}$—CH=C(I)—$C_6F_{13}$ $C_8F_{17}$—CH=C(I)—$C_2F_5$ $C_6F_{13}$—CH=C(I)—$C_2F_5$ $C_8F_{17}$—CH=C(I)—$C_8F_{17}$ $C_4F_9$—CH=C(I)—$C_8F_{17}$ i—$C_3F_7$—CH=C(I)—$C_4F_9$

Each of the composition were intraperitoneally injected into mice at doses of 50 g/kg. All of the mice so injected survived and were alive past the end of the protocol, 30 days post injection.

We also measured the radiopacity of each of the compositions using the in vitro test described in Example 1, where 0.34 mol/L solutions of the compositions were prepared in hexane and scanned using a Philips Tomoscan LX 120 kV, 175 mA apparatus. Each of the products showed greater radiopacity than a PFOB control (FIG. 1) (right lane).

The results of the above examples show that the compositions of the invention have about 4 times more radiopacity, in vitro, than that of perfluorooctyl bromide, and, in the form of in vivo emulsions, 5 to 7 times more radiopacity than the contrast-power of a concentrated emulsion of perfluorooctyl bromide.

The compositions of the invention are thus of great interest as contrast agents. Moreover, these compositions are surprisingly biocompatible, both in pure form and in the form of an emulsion; this differentiates them from the iodinated fluorinated compounds of the prior art. Moreover, appropriate contrast enhancement dosages will, therefore, be readily apparent to those of ordinary skill in the art.

While the present invention has been described in the context of a variety of preferred embodiments, the foregoing is illustrative rather than limiting. Therefore, the scope of the invention should only be construed with reference to the appended claims and any equivalents thereof.

What we claim is:

1. A dispersion, emulsion, microemulsion, or gel composition comprising:
   an oily phase comprising a radiographically imageable amount of an iodinated fluorinated organic compound, wherein the compound is not terminally iodinated;
   an essentially aqueous phase; and
   a surfactant.

2. The composition of claim 1, wherein the iodinated fluorinated compound is of the following general structure:

$R_FCH=CIR^1$ wherein,
   $R_F$ is a linear, branched, or cyclic first fluorocarbon radical, having 2 to 12 carbon atoms in which 50 to 100% of the hydrogen atoms have been replaced by fluorine atoms; and
   $R^1$ is selected from the group consisting of a second fluorocarbon radical and a hydrocarbon radical, wherein,
      the second fluorocarbon radical is linear, branched, or cyclic, having 2 to 12 carbon atoms in which 50 to 100% of the hydrogen atoms have been replaced by fluorine atoms; and
      the hydrocarbon radical is linear, branched, or cyclic, having 2 to 14 carbon atoms.

3. The composition of claim 2, wherein any of the fluorocarbon radicals additionally comprises one or more hydrogen atoms replaced by a halogen atom other than fluorine.

4. The composition of claim 2, wherein $R_F$ additionally comprises a heteroatom selected from the group consisting of oxygen and sulfur substituted in or on the radical.

5. The composition of claim 2, wherein $R^1$ additionally comprises a heteroatom selected from the group consisting of oxygen and sulfur substituted in or on the radical.

6. The composition of claim 2, wherein:

the first fluorocarbon radical is selected from the group consisting of $F(CF_2)_i$— where i is an integer from 2 to 12, $(CF_3)_2CF$—$(CF_2)_j$— where j is an integer from 0 to 8, and $CF_3$—$[CF_2CF(CF_3)]_k$— where k is an integer from 1 to 4, $C_2F_5$—$[CF_2CF(CF_3)]_k$— where k is an integer from 1 to 4, $(CF_3)_2CF$—$[CF_2CF(CF_3)]_k$— where k is an integer from 1 to 4, $(R_{F2})(R_{F3})CFO(CF_2$—$CF_2)L$ where $R_{F2}$ and $R_{F3}$ independently represent a moiety selected from the group consisting of $CF_3$—, $C_2F_5$—, n—$C_3F_7$—, and $CF_3CF_2CF(CF_3)$— where L is an integer from 1 to 6, $(R_{F2})(R_{F3})CFO(CF_2$—$CF_2)L$ where $R_{F2}$ and $R_{F3}$ together form —$(CF_2)_4$— or —$(CF_2)_5$— and where L is an integer from 1 to 6, $CF_3CF_2O[CF_2CF_2O]_mCF_2$— where m is an integer from 0 to 5, and $CF_3(CF_2)_2O([CF(CF_3)CF_2O]_n$—$CF(CF_3)$— where n is an integer from 0 to 6;

the second fluorocarbon radical is selected from the group consisting of $F(CF_2)_i$— where i is an integer from 2 to 12, $(CF_3)_2CF$—$(CF_2)_j$— where j is an integer from 0 to 8, and $CF_3$—$[CF_2CF(CF_3)]_k$— where k is an integer from 1 to 4, $C_2F_5$—$[CF_2CF(CF_3)]_k$— where k is an integer from 1 to 4, $(CF_3)_2CF$—$[CF_2CF(CF_3)]_k$— where k is an integer from 1 to 4, $(R_{F2})(R_{F3})CFO(CF_2$—$CF_2)L$ where $R_{F2}$ and $R_{F3}$ independently represent a moiety selected from the group consisting of $CF_3$—, $C_2F_5$—, n—$C_3F_7$—, and $CF_3CF_2CF(CF_3)$— where L is an integer from 1 to 6, $(R_{F2})(R_{F3})CFO(CF_2$—$CF_2)L$ where $R_{F2}$ and $R_{F3}$ together form —$(CF_2)_4$— or —$(CF_2)_5$— and where L is an integer from 1 to 6, $CF_3CF_2O[CF_2CF_2O]_mCF_2$— where m is an integer from 0 to 5, and $CF_3(CF_2)_2O([CF(CF_3)CF_2O]_n$—$CF(CF_3)$— where n is an integer from 0 to 6; and the hydrocarbon radical is selected from the group consisting of $CH_3$—$(CH_2)_{y1}$— wherein $y_1$ is an integer between 1 and 15, $CH_3$—$(CH_2)_{y2}(CH$=$CH)_q(CH_2)_{y3}$ wherein y2 is an integer between 1 and 15, q=0 or 1, and y3 is an integer between 0 and 15, $CH_3(CH_2)_{y7}$ in which y7 is an integer between 1 and 11, $CH_3$—$(CH_2)_{y2}$—S—$(CH_2)_{y4}$— wherein y2 is an integer between 1 and 15 and y4 is an integer between 1 and 15, $CH_3$—$(CH_2$—$CH_2O)_{y5}$—$CH_2$— wherein y5 is an integer between 1 and 8, and $CH_3$—$(CH(CH_3)CH_2O)_{y6}$—$CH(CH_3)$— wherein y6 is an integer between 1 and 11.

7. The composition of claim 2, wherein $R_F$ is $F(CF_2)_i$ in which i is an integer between 2 and 12 and $R^1$ is $CH_3(CH_2)_{y7}$ in which y7 is an integer between 1 and 11.

8. The composition of claim 7, wherein the oily phase comprises $C_6F_{13}$—CH=C(I)—$C_6H_{13}$.

9. The composition of claim 7, wherein the oily phase comprises $C_8F_{17}$—CH=C(I)—$C_8H_{17}$.

10. The composition of claim 1, wherein the surfactant is selected from the group consisting of copolymers of polyoxyethylene-polyoxypropylene, sorbitan polyoxyethylenes, and perfluorinated surfactans.

11. The composition of claim 1, wherein the surfactant is lecithin.

12. The composition of claim 1, wherein the aqueous phase additionally comprises one or more additives.

13. The composition of claim 12, wherein the additive is selected from the group consisting of mineral salts, buffers, osmotic or oncotic agents, pharmaceuticals, nutritive products, and anti-oxidants.

14. The composition of claim 2 or 6, wherein the ratio of the oily phase, aqueous phase, and surfactant comprise:

from 10 to 120% weight/volume of the oily phase;

from 0.1 to 10% weight/volume of the surfactant; and the aqueous phase forming the balance.

15. The composition of claim 14, wherein the composition is in the form of an emulsion.

16. The composition of claim 15, wherein the composition is in the form of a microemulsion.

17. A composition for biomedical use comprising an iodinated fluorinated compound in a fluorocarbon carrier, wherein the compound has the following general structure:

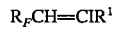

wherein, $R_F$ is a linear, branched, or cyclic first fluorocarbon radical, having 2 to 12 carbon atoms in which 50 to 100% of the hydrogen atoms have been replaced by fluorine atoms; and $R^1$ is selected from the group consisting of a second fluorocarbon radical and a hydrocarbon radical, wherein, the second fluorocarbon radical is linear, branched, or cyclic, having 2 to 12 carbon atoms in which 50 to 100% of the hydrogen atoms have been replaced by fluorine atoms; and the hydrocarbon radical is linear, branched, or cyclic, having 2 to 14 carbon atoms.

18. The composition of claim 17, wherein:

the first fluorocarbon radical is selected from the group consisting of $F(CF_2)_i$— where i is an integer from 2 to 12, $(CF_3)_2CF$—$(CF_2)_j$— where j is an integer from 0 to 8, and $CF_3$—$[CF_2CF(CF_3)]_k$— where k is an integer from 1 to 4, $C_2F_5$—$[CF_2CF(CF_3)]_k$— where k is an integer from 1 to 4, $(CF_3)_2CF$—$[CF_2CF(CF_3)]_k$— where k is an integer from 1 to 4, $(R_{F2})(R_{F3})CFO(CF_2$—$CF_2)L$ where $R_{F2}$ and $R_{F3}$ independently represent a moiety selected from the group consisting of $CF_3$—, $C_2F_5$—, n—$C_3F_7$—, and $CF_3CF_2CF(CF_3)$— where L is an integer from 1 to 6, $(R_{F2})(R_{F3})CFO(CF_2$—$CF_2)L$ where $R_{F2}$ and $R_{F3}$ together form —$(CF_2)_4$— or —$(CF_2)_5$— and where L is an integer from 1 to 6, $CF_3CF_2O[CF_2CF_2O]_mCF_2$— where m is an integer from 0 to 5, and $CF_3(CF_2)_2O([CF(CF_3)CF_2O]_n$—$CF(CF_3)$— where n is an integer from 0 to 6;

the second fluorocarbon radical is selected from the group consisting of $F(CF_2)_i$— where i is an integer from 2 to 12, $(CF_3)_2CF$—$(CF_2)_j$— where j is an integer from 0 to 8, and $CF_3$—$[CF_2CF(CF_3)]_k$— where k is an integer from 1 to 4, $C_2F_5[CF_2CF(CF_3)]_k$— where k is an integer from 1 to 4, $(CF_3)_2CF$—$[CF_2CF(CF_3)]_k$— where k is an integer from 1 to 4, $(R_{F2})(R_{F3})CFO(CF_2$—$CF_2)L$ where $R_{F2}$ and $R_{F3}$ independently represent a moiety selected from the group consisting of $CF_3$—, $C_2F_5$—, n—$C_3F_7$—, and $CF_3CF_2CF(CF_3)$— where L is an integer from 1 to 6, $(R_{F2})(R_{F3}CFO(CF_2$—$CF_2)L$ where $R_{F2}$ and $R_{F3}$ together form —$(CF_2)_4$— or —$(CF_2)_5$— and where L is an integer from 1 to 6, $CF_3CF_2O[CF_2CF_2O]_mCF_2$— where m is an integer from 0 to 5, and $CF_3(CF_2)_2O([CF(CF_3)CF_2O]_n$—$CF(CF_3)$— where n is an integer from 0 to 6; and the hydrocarbon radical is selected from the group consisting of $CH_3—(CH_2)_{y1}—$ wherein $y_1$ is an integer between 1 and 15, $CH_3—(CH_2)_{y2}(CH=CH)_q(CH_2)_{y3}$ wherein y2 is an integer between 1 and 15, q=0 or 1, and y3 is an integer between 0 and 15, $CH_3(CH_2)_{y7}$ in which y7 is an integer between 1 and 11, $CH_3—(CH_2)_{y2}—S—(CH_2)_{y4}—$ wherein y2 is an integer between 1 and 15 and y4 is an integer between 1 and 15, $CH_3—(CH_2—CH_2—O)_{y5}—CH_2—$ wherein y5 is an integer between 1 and 8, and $CH_3—(CH(CH_3)CH_2O)_{y6}—CH(CH_3)—$ wherein y6 is an integer between 1 and 11.

19. The composition of claim 18, wherein $R_F$ is $F(CF_2)_i$ in which i is an integer between 2 and 12 and $R^1$ is $CH_3(CH_2)_{y7}$ in which y7 is an integer between 1 and 11.

20. The composition of claim 19, wherein the compound is $C_6F_{13}—CH=C(I)—C_6H_{13}$.

21. The composition of claim 19, wherein the compound is $C_8F_{17}—CH=C(I)—C_8H_{17}$.

22. The composition of claim 17, wherein the fluorocarbon carrier is selected from the group consisting of perfluorodecalin, perfluorooctyl bromide, perfluorodecyl bromide and 1,2-bis-F-alkylethenes.

23. A contrast agent for use in radiography comprising the composition of claim 17.

24. A contrast agent for use in scintigraphy comprising the composition of claim 17, wherein the iodine atom is a radioactive iodine atom selected from the group consisting of iodine-123, iodine-125, and iodine-131.

25. An emulsion, comprising:
an oily phase comprising a radiographically imageable amount of an iodinated fluorinated compound of the following general structure:

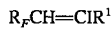

wherein,
$R_F$ is a linear, branched, or cyclic first fluorocarbon radical having 2 to 12 carbon atoms selected from the group consisting of $F(CF_2)_i—$ where i is an integer from 2 to 12, $(CF_3)_2CF—(CF_2)_j—$ where j is an integer from 0 to 8, and $CF_3—[CF_2CF(CF_3)]_k—$ where k is an integer from 1 to 4, $C_2F_5—[CF_2CF(CF_3)]_k—$ where k is an integer from 1 to 4, $(CF_3)_2CF—[CF_2CF(CF_3)]_k—$ where k is an integer from 1 to 4, $(R_{F2})(R_{F3})CFO(CF_2—CF_2)L$ where $R_{F2}$ and $R_{F3}$ independently represent a moiety selected from the group consisting of $CF_3—$, $C_2F_5—$, $n—C_3F_7—$, and $CF_3CF_2CF(CF_3)—$ where L is an integer from 1 to 6, $(R_{F2})(R_{F3})CFO(CF_2—CF_2)L$ where $R_{F2}$ and $R_{F3}$ together form $—(CF_2)_4—$ or $—(CF_2)_5—$ and where L is an integer from 1 to 6, $CF_3CF_2O[CF_2CF_2O]_mCF_2—$ where m is an integer from 0 to 5, and $CF_3(CF_2)_2O([CF(CF_3)CF_2O]_n—CF(CF_3)—$ where n is an integer from 0 to 6;
$R^1$ is selected from the group consisting of a linear, branched, or cyclic second fluorocarbon radical having 2 to 12 carbon atoms and a linear, branched, or cyclic hydrocarbon radical having 2 to 14 carbon atoms, wherein,
the second flurocarbon radical is selected from the group consisting of $F(CF_2)_i—$ where i is an integer from 2 to 12, $(CF_3)_2CF—(CF_2)_j—$ where j is an integer from 0 to 8, and $CF_3—[CF_2CF(CF_3)]_k—$ where k is an integer from 1 to 4, $C_2F_5—[CF_2CF(CF_3)]_k—$ where k is an integer from 1 to 4, $(CF_3)_2CF—[CF_2CF(CF_3)]_k—$ where k is an integer from 1 to 4, $(R_{F2})(R_{F3})CFO(CF_2—CF_2)L$ where $R_{F2}$ and $R_{F3}$ independently represent a moiety selected from the group consisting of $CF_3—$, $C_2F_5—$, $n—C_3F_7—$, and $CF_3CF_2CF(CF_3)—$ where L is an integer from 1 to 6, $(R_{F2})(R_{F3})CFO(CF_2—CF_2)L$ where $R_{F2}$ and $R_{F3}$ together form $—(CF_2)_4—$ or $—(CF_2)_5—$ and where L is an integer from 1 to 6, $CF_3CF_2O[CF_2CF_2O]_mCF_2—$ where m is an integer from 0 to 5, and $CF_3(CF_2)_2O([CF(CF_3)CF_2O]_n—CF(CF_3)—$ where n is an integer from 0 to 6; and
the hydrocarbon radical is selected from the group consisting of $CH_3—(CH_2)_{y1}—$ wherein $y_1$ is an integer between 1 and 15, $CH_3—(CH_2)_{y2}(CH=CH)_q(CH_2)_{y3}$ wherein y2 is an integer between 1 and 15, q=0 or 1, and y3 is an integer between 0 and 15, $CH_3(CH_2)_{y7}$ in which y7 is an integer between 1 and 11, $CH_3—(CH_2)_{y2}—S—(CH_2)_{y4}—$ wherein y2 is an integer between 1 and 15 and y4 is an integer between 1 and 15, $CH_3—(CH_2—CH_2—O)_{y5}—CH_2—$ wherein y5 is an integer between 1 and 8, and $CH_3—(CH(CH_3)CH_2O)_{y6}—CH(CH_3)—$ wherein y6 is an integer between 1 and 11;
an essentially aqueous phase; and
a surfactant.

26. The emulsion of claim 25, wherein $R_F$ is $F(CF_2)_i$ in which i is an integer between 2 and 12 and $R^1$ is $CH_3(CH_2)_{y7}$ in which y7 is an integer between 1 and 11.

27. The emulsion of claim 26, wherein the oily phase comprises $C_6F_{13}—CH=C(I)—C_6H_{13}$.

28. The emulsion of claim 26, wherein the oily phase comprises $C_8F_{17}—CH=C(I)—C_8H_{17}$.

29. The emulsion of claim 25, wherein the surfactant is selected from the group consisting of copolymers of polyoxyethylene-polyoxypropylene, sorbitan polyoxyethylenes, and perfluorinated surfactants.

30. The emulsion of claim 25, wherein the surfactant is lecithin.

31. The emulsion of claim 25, wherein the aqueous phase additionally comprises one or more additives.

32. The emulsion of claim 31, wherein the additive is selected from the group consisting of mineral salts, buffers, osmotic or onocotic agents, pharmaceuticals, nutritive products, and anti-oxidants.

33. A method for performing a radiographic procedure, comprising:
administering a radiographic contrast enhancement effective amount of an iodinated fluorinated compound to a patient, wherein the compound has the following general structure:

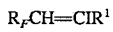

wherein,
$R_F$ is a linear, branched, or cyclic first fluorocarbon radical, having 2 to 12 carbon atoms in which 50 to 100% of the hydrogen atoms have been replaced by fluorine atoms; and
$R^1$ is selected from the group consisting of a second fluorocarbon radical and a hydrocarbon radical, wherein,
the second fluorocarbon radical is linear, branched, or cyclic, having 2 to 12 carbon atoms in which 50 to 100% of the hydrogen atoms have been replaced by fluorine atoms; and
the hydrocarbon radical is linear, branched, or cyclic, having 2 to 14 carbon atoms.

34. The method of claim 33, wherein:

the first fluorocarbon radical is selected from the group consisting of $F(CF_2)_i$— where i is an integer from 2 to 12, $(CF_3)_2CF$—$(CF_2)_j$— where j is an integer from 0 to 8, and $CF_3$—$[CF_2CF(CF_3)]_k$— where k is an integer from 1 to 4, $C_2F_5$—$[CF_2CF(CF_3)]_k$— where k is an integer from 1 to 4, $(CF_3)_2CF$—$[CF_2CF(CF_3)]_k$— where k is an integer from 1 to 4, $(R_{F2})(R_{F3})CFO(CF_2$—$CF_2)L$ where $R_{F2}$ and $R_{F3}$ independently represent a moiety selected from the group consisting of $CF_3$—, $C_2F_5$—, n—$C_3F_7$—, and $CF_3CF_2CF(CF_3)$— where L is an integer from 1 to 6, $(R_{F2})(R_{F3})CFO(CF_2$—$CF_2)L$ where $R_{F2}$ and $R_{F3}$ together form —$(CF_2)_4$— or —$(CF_2)_5$— and where L is an integer from 1 to 6, $CF_3CF_2O[CF_2CF_2O]_mCF_2$— where m is an integer from 0 to 5, and $CF_3(CF_2)_2O([CF(CF_3)CF_2O]_n$—$CF(CF_3)$— where n is an integer from 0 to 6;

the second fluorocarbon radical is selected from the group consisting of $F(CF_2)_i$— where i is an integer from 2 to 12, $(CF_3)_2CF$—$(CF_2)_j$— where j is an integer from 0 to 8, and $CF_3$—$[CF_2CF(CF_3)]_k$— where k is an integer from 1 to 4, $C_2F_5$—$[CF_2CF(CF_3)]_k$— where k is an integer from 1 to 4, $(CF_3)_2CF$—$[CF_2CF(CF_3)]_k$— where k is an integer from 1 to 4, $(R_{F2})(R_{F3})CFO(CF_2$—$CF_2)L$ where $R_{F2}$ and $R_{F3}$ independently represent a moiety selected from the group consisting of $CF_3$—, $C_2F_5$—, n—$C_3F_7$—, and $CF_3CF_2CF(CF_3)$— where L is an integer from 1 to 6, $(R_{F2})(R_{F3})CFO(CF_2$—$CF_2)L$ where $R_{F2}$ and $R_{F3}$ together form —$(CF_2)_4$— or —$(CF_2)_5$— and where L is an integer from 1 to 6, $CF_3CF_2O[CF_2CF_2O]_mCF_2$— where m is an integer from 0 to 5, and $CF_3(CF_2)_2O([CF(CF_3)CF_2O]_n$—$CF(CF_3)$— where n is an integer from 0 to 6; and the hydrocarbon radical is selected from the group consisting of $CH_3$—$(CH_2)_{y1}$— wherein $y_1$ is an integer between 1 and 15, $CH_3$—$(CH_2)_{y2}(CH$=$CH)_q(CH_2)_{y3}$ wherein y2 is an integer between 1 and 15, q=0 or 1, and y3 is an integer between 0 and 15, $CH_3(CH_2)_{y7}$ in which y7 is an integer between 1 and 11, $CH_3$—$(CH_2)_{y2}$—S—$(CH_2)_{y4}$— wherein y2 is an integer between 1 and 15 and y4 is an integer between 1 and 15, $CH_3$—$(CH_2$—$CH_2$—$O)_{y5}$—$CH_2$— wherein y5 is an integer between 1 and 8, and $CH_3$—$(CH(CH_3)CH_2O)_{y6}$—$CH(CH_3)$— wherein y6 is an integer between 1 and 11.

35. The method of claim 34, wherein $R_F$ is $F(CF_2)_i$ in which i is an integer between 2 and 12 and $R^1$ is $CH_3(CH_2)_{y7}$ in which y7 is an integer between 1 and 11.

36. The method of claim 35, wherein the compound is $C_6F_{13}$—CH=C(I)—$C_6H_{13}$.

37. The method of claim 35, wherein the compound is $C_8F_{17}$—CH=C(I)—$C_8H_{17}$.

38. The method of claim 33, wherein any of the fluorocarbon radicals assitionally comprises one or more hydrogen atoms replaced by a halogen atom other than fluorine.

39. The method of claim 33, wherein $R_F$ additionally comprises a heteroatom selected from the group consisting of oxygen and sulfur substituted in or on the radical.

40. The method of claim 33, wherein $R^1$ additionally comprises a heteroatom selected from the group consisting of oxygen and sulfur substituted in or on the radical.

* * * * *